United States Patent
Hussain et al.

(10) Patent No.: US 8,745,721 B2
(45) Date of Patent: Jun. 3, 2014

(54) MESSAGING SYSTEM FOR HEALTHCARE COMMUNITY

(71) Applicants: Zakir Hussain, Scarborough (CA);
Suhail Syed, Scarborough (CA);
Rizwana Banu, Sarborough (CA);
Humayun Salim Asghar, Scarborough (CA)

(72) Inventors: Zakir Hussain, Scarborough (CA);
Suhail Syed, Scarborough (CA);
Rizwana Banu, Sarborough (CA);
Humayun Salim Asghar, Scarborough (CA)

(73) Assignee: Velo Mobile Health, Inc., Markham, Ontario (CA)

( * ) Notice: Subject to any disclaimer, the term of this patent is extended or adjusted under 35 U.S.C. 154(b) by 5 days.

(21) Appl. No.: 13/633,049

(22) Filed: Oct. 1, 2012

(65) Prior Publication Data

US 2014/0096225 A1    Apr. 3, 2014

(51) Int. Cl.
*G06F 15/16* (2006.01)
*G06F 17/00* (2006.01)
*G06F 9/00* (2006.01)
*H04L 12/28* (2006.01)
*H04L 12/56* (2006.01)

(52) U.S. Cl.
USPC .............................. 726/11; 709/206; 370/401

(58) Field of Classification Search
USPC ........................ 713/153–154; 726/2–3, 11–15;
709/204–207, 249, 246–247
See application file for complete search history.

(56) References Cited

U.S. PATENT DOCUMENTS

2004/0092250 A1* 5/2004 Valloppillil ................ 455/412.1
2009/0164252 A1* 6/2009 Morris et al. ...................... 705/3

* cited by examiner

*Primary Examiner* — Ashokkumar Patel
*Assistant Examiner* — Evans Desrosiers
(74) *Attorney, Agent, or Firm* — Douglas L. Weller

(57) ABSTRACT

A messaging system for a health care community includes a private network. Electronic medical records are accessible via the private network. A calendar system includes appointments of patients with medical providers. An encrypted firewall and subscriber directory limits access to the private network so that only subscribers to the private network have access to the private network. Subscribers are identified by mobile phone numbers or extensions.

13 Claims, 4 Drawing Sheets

MESSAGING SYSTEM FOR HEALTHCARE COMMUNITY

BACKGROUND

Paper-based records are often used to record patient information. While paper-based records provide for ease of data entry and low cost, they require a significant amount of storage space compared to digital records. Handwritten paper medical records can also be difficult to read increasing the potential for medical errors.

Electronic medical records (EMRs) are an alternative to paper-based records. EMRs are often part of a local stand-alone health information system that allows storage, retrieval and modification of records.

EMRs allow for continuously updating. When EMRs can be exchanged between different EMR systems, this facilitates the co-ordination of healthcare delivery in non-affiliated healthcare facilities. Additionally, EMRs can be used to generate anonymous statistical information that can be used to improve quality of care, resource management and disease surveillance.

DETAILED DESCRIPTION

Figure 1:
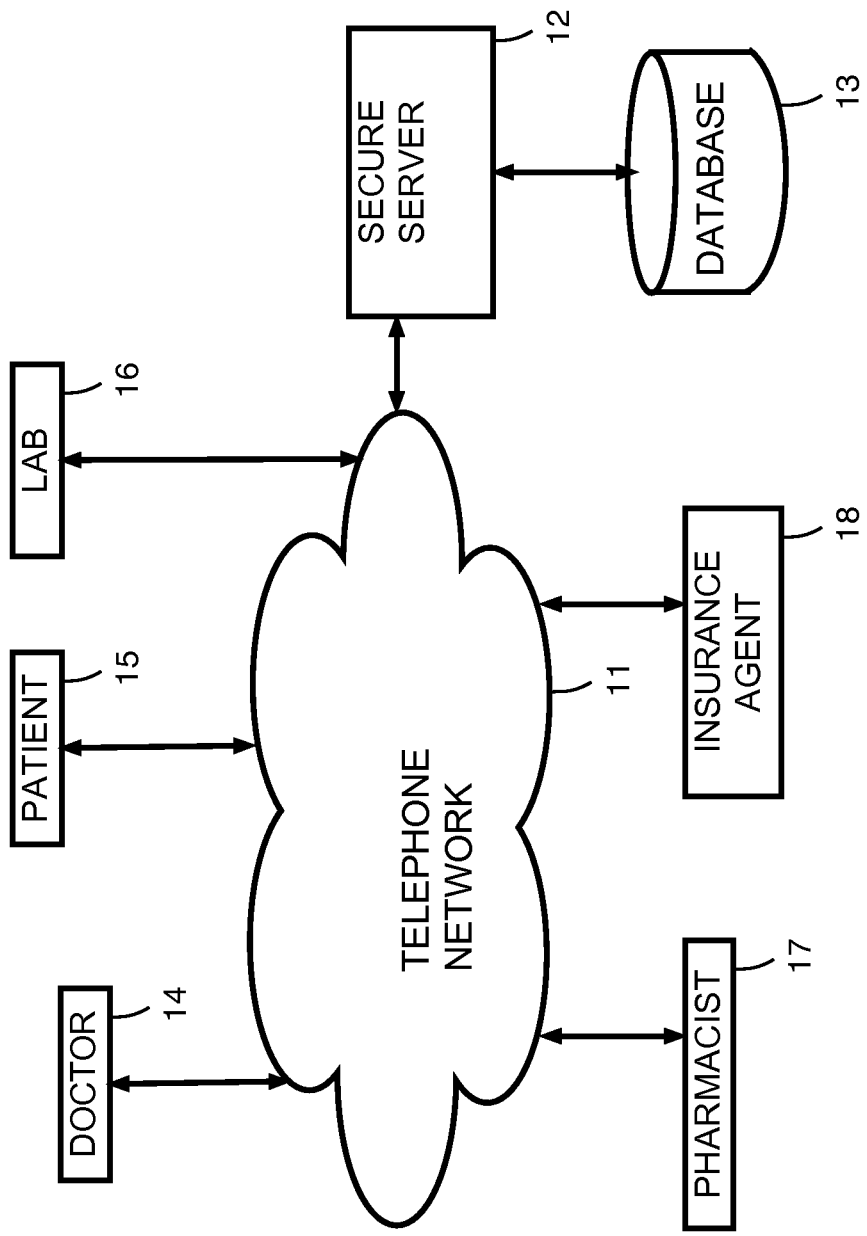
FIG. 1 and FIG. 2 are block diagrams illustrating a messaging system for a healthcare community in accordance with an implementation.

FIG. 1 is a block diagram illustrating a medical community in contact via a telephone network 11. The medical community can include any entity that is involved in providing or facilitating medical care to a patient 15. For example, FIG. 1 shows a doctor 14, a lab 16, a pharmacist 17 and an insurance agent 18 all able to communicate over a telephone network 11. Medical records and other data related to patient care, billing and so on, are stored within a secure server 12 with access to a database 13.

Figure 2:
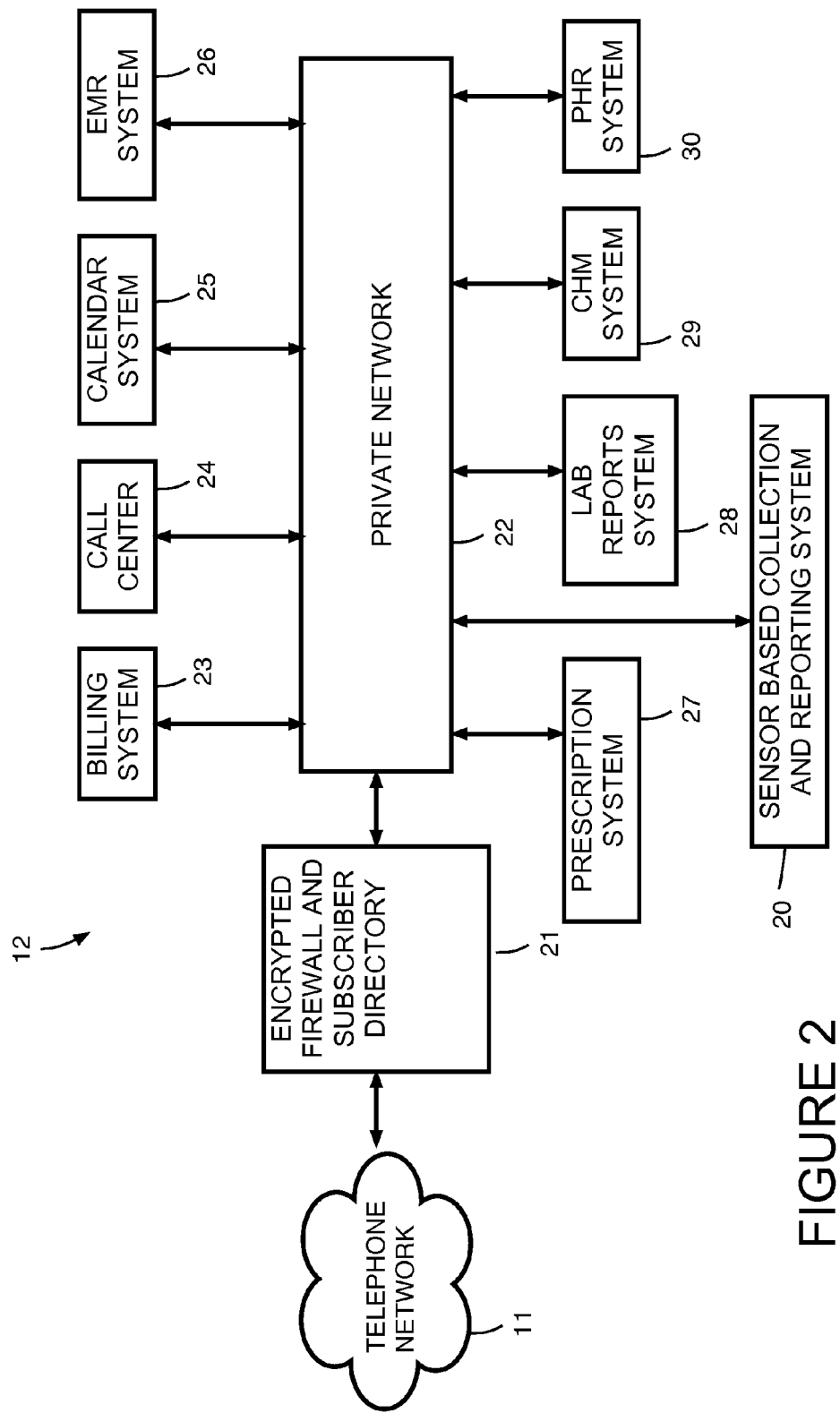

FIG. 2 provides an example block diagram of secure server 12. For example, secure server 12 is shown to include an encrypted firewall and subscriber director 21. For example, encrypted firewall and subscriber director 21 limits access to a private network 22, implemented by secure server 12. Only subscribers to private network 22 are allowed access to private network 22. For example, encrypted firewall and subscriber director 21 identifies subscribers by their mobile numbers or extensions. Alternatively, subscribers may additionally be required to provide passwords or other identification to gain access to messaging system through encrypted firewall and subscriber directory 21. For example, any or all of doctor 14, lab 16, pharmacist 17 and insurance agent 18 could be registered as subscribers to private network 22. Patient 15 can also be registered as a subscriber to private network 22.

Private network 22 allows for messages to be sent to and from, for example, a billing system 23, a call center 24, a calendar system 25, an EMR system 26 a prescription system 27, lab reports system 28, a chronic health management (CHM) system 29, a personal health record (PHR) system 30.

Communication over private network 22 is performed using wireless mobile numbers, mobile enabled numbers, or uniquely assigned numbers to identify senders and receivers of messages. Alternatively, or in addition, other forms of identifiers can be used to identify subscribers to the network. These other forms of identifiers can be, for example, a national identification card number, a medical office number, a social security number, an system generated unique alphanumeric identifier, and so on. Messages can be, for example, in the form of short message service (SMS), multimedia message service (MMS), e-mail, fax, voice, instant message (IM) and video.

Encrypted firewall and subscriber directory 21 is connected to telephone network 11, for example, via a direct private encrypted interconnection to a mobile carrier. Communication via the direct private encrypted interconnection is, for example, through short message peer-to-peer (SMPP), virtual private network (VPN), hypertext transfer protocol (HTTP), into a short message service center implemented by private network 22. Messages received by private network 22 are verified, authenticated and forwarded to a register subscriber. For example, when a subscriber originates an SMS message sent to private network 22, the subscriber is verified against credit status to determine whether the subscriber is authorized to initiate messages sent through private network 22. For example, when patients are listed as subscribers to the system, this allows the patients SMS access to their health providers through private network 22. This SMS access is provided only when the patients are listed as subscribers.

For example, a global system for mobile communications (GSM) receives a mobile originated (MO) SMS, checks the originator of the MO-SMS against the mobile number range assigned within private network 22. If the originator is within the mobile number ranged assigned the MO-SMS is forwarded to private network 22. Private network 22 acts, for example, as a short message service center (SMSC) to deliver the MO-SMS. SMS gateways are used to connect private network 22 to other SMSCs. A mobile terminated (MT) SMS from within private network 22 can thus be forwarded to entities connected to other SMSCs.

For example, private network 22 maintains detailed system logs of all activity within private network 22 to protect against data deletions or breaches. Any such deletions or breaches are reported to a system administrator.

Figure 3:
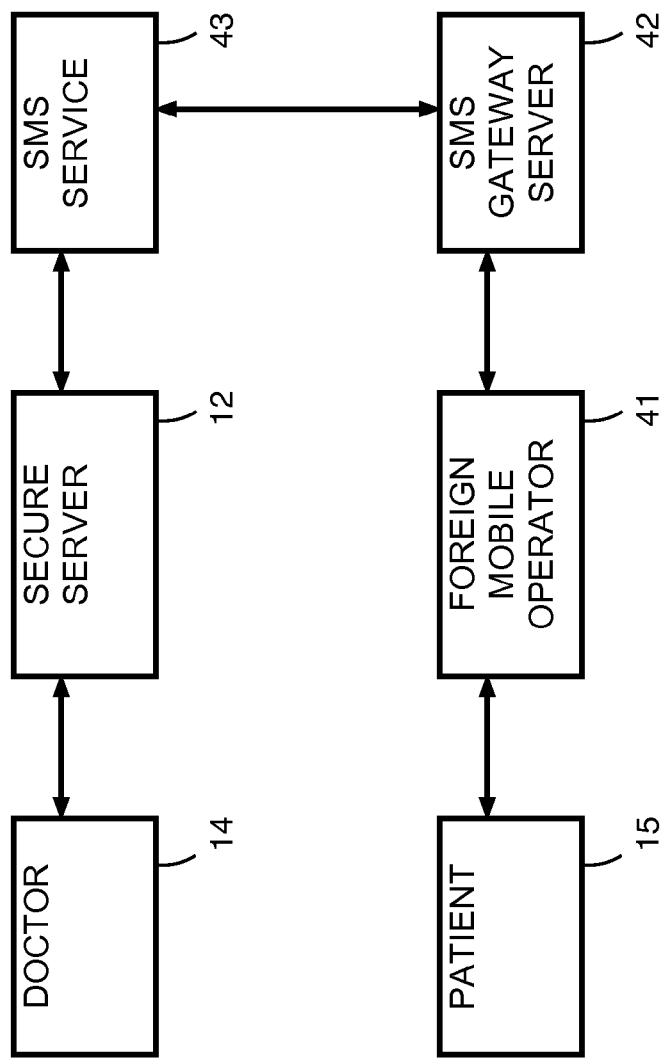
FIG. 3 is a block diagrams providing additional information about blocks used to facilitate short message service communication (SMS) in accordance with an implementation.

FIG. 3 provides additional information about blocks used to facilitate SMS communication, for example, with calendar system 25 or other system hosted within server 12. Doctor 14, or another client such as a receptionist, accesses server 12 from any latest compatible web browser. Doctor 14 uses server 12 to send SMS, to manage sent and received SMS, to create and view SMS reminders, to add and manage contacts, to add and manage patient contact details, to categorize patients into groups and perform group management, to create and view SMS templates, to do online payment, to view billing, to view current SMS rates, to manage client profile settings, to create and view appointments on a calendar or any other allowed functionality implemented within server 12, for example, by billing system 23, call center 24, calendar system 25, EMR system 26 PHR system 30, CHM system 29, lab reports block 28 and prescription system 27 (all shown in FIG. 2) or any other system implemented within server 12.

Doctor 14 and other clients of server 12 each has a unique extension identifier. For example, server 12 hosts a main application that processes all client requests, collects general and SMS specific data and saves in this information in database a database such as a MySQL 5.5. server.

SMS service 44 is implemented, for example, by windows based clients. For example SMS related APIs from InetLab are used to push and pull SMS from a SMS gateway 42. For example, SMS service 43 supports two kinds of SMS services: SMS transmission and SMS reception. For example, SMS transmitter clients work independently at different levels. One client does SMS data spooling from database and another client sends the spooled SMS to SMS Gateway 42 to avoid a complete burden on a single client. For example, SMS receiver clients pull SMS from SMS Gateway 42 and forward the SMS into a database based on the extensions received. For example, SMS receiver clients use SMPP APIs and HTTP Protocols from Inetlab to receive and process SMS.

SMS gateway server 42 handles all backend SMS related operations like customer and vendor connector configurations, customer and vendor user credentials, routing details, billing details, rates, SMS logs, delivery reports, and so on. SMS gateway server 42 is responsible to forward and route received SMS to respective mobile operators.

A foreign mobile operator 41 receives SMS from SMS gateway server 42 and further process the SMS to send to an end user such as patient 15.

Calendaring system 25 is available, for example, to those with a user account on server 12. A logged on user can view a personal counter presented as a web page and displayed by a web browser. Calendar appointments can be requested and obtained via SMS for those that know the extension of a user of calendaring system 25.

Figure 4:
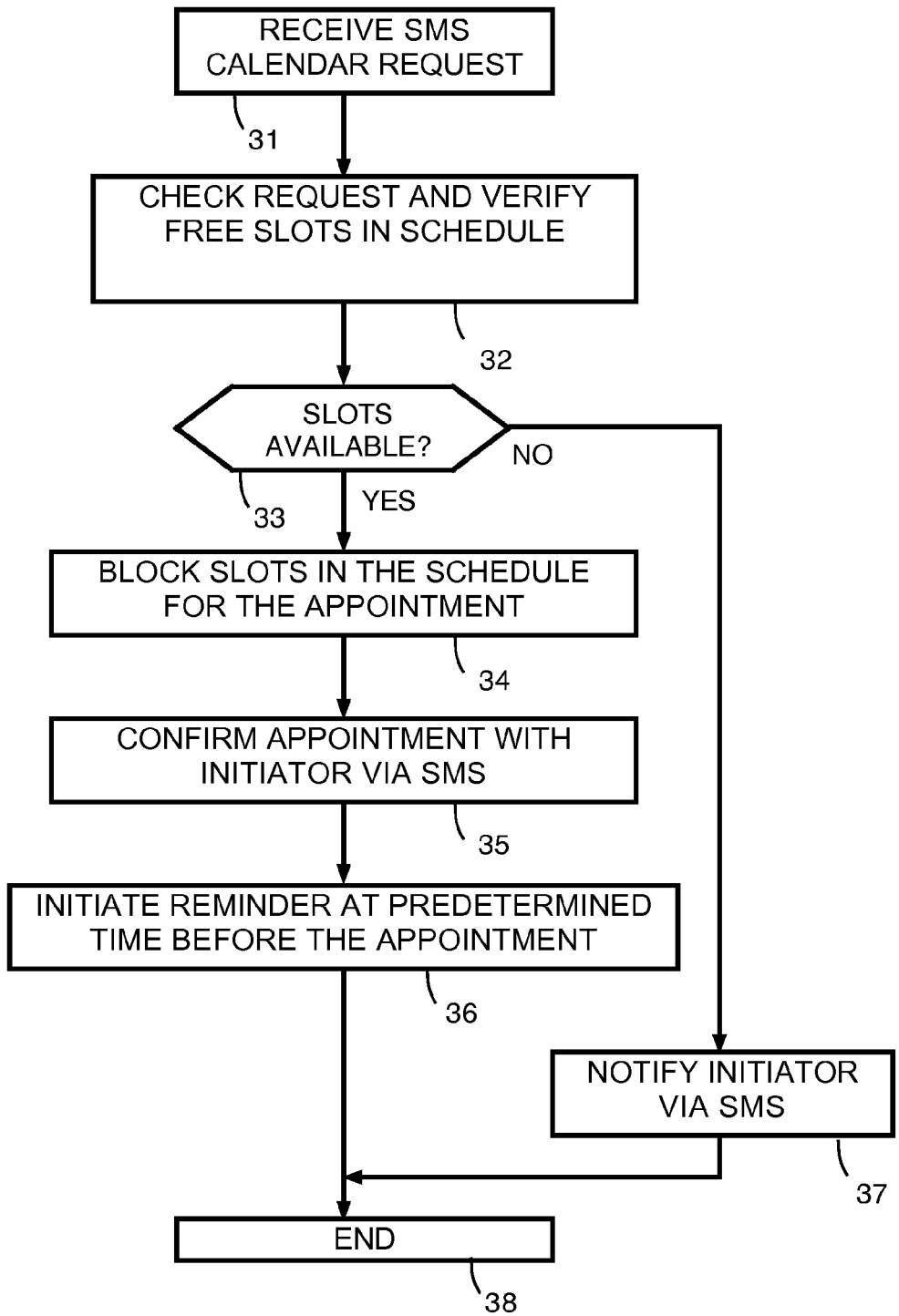
FIG. 4 is a simplified flowchart showing use of SMS to perform calendaring of appointments in accordance with an implementation.

For example, FIG. 4 is a simplified flowchart showing use of SMS by subscribers to perform calendaring of appointments. In a block 31, an appointment request is received by calendar system 25. For example, the appointment request is initiated from a mobile phone or other entity capable of sending SMS messaging. The appointment request in received by encrypted firewall and subscriber directory 21. After encrypted firewall and subscriber director 21 identifies the initiator as a subscriber of the system, private network 22 verifies, authenticates and forwards the appointment request to calendar system 25. For example, when patients are listed as subscribers to the system for the purpose of scheduling appointments, this allows patients to schedule their own appointments.

In a block 32, calendar system 25 checks the request and verifies there are free slots in the identified schedule to accommodate the appointment request. If, in a block 33, it is determine slots are not available, in a block 37, calendar system 25 so notifies the initiator via SMS. In a block 38, handling of the calendaring is completed.

Users of calendar system 25 can view, edit and change multiple calendars based on user access privileges allocated through an administrator. The complete history of calendar changes is saved and changes are communicated through SMS. Appointments are visually prioritized, for example, as per a defined triage system. The triage system, for example, uses a predefined color coding system to indicate priority level of appointments. For example, high priority appointments are listed in one color on a calendar, lower priority apartments are listed in another color on the calendar, lowest priority appointments are listed in a third color on the calendar, and so on. An authorized user of calendar system 25 can alter the triage system based on appointment requests.

If in block 33 it is determined slots are available, in a block 34, slots in the schedule are blocked out for the appointment. In a block 35, the appointment is confirmed by calendar system 25 sending an SMS notification to the initiator. At a predetermined time before the appointment, e.g. 24 hours before the appointment, calendar system 25 sends, via SMS, a reminder to the initiator of the upcoming appointment.

Patient 15 sends and receives SMS using, for example, a mobile device. For example, any SMS received by patient 15 will be received from a shortcode number and the message will be prefixed with a doctor's extension. Also, for example, any SMS that patient 15 sends the doctor's office is sent to a shortcode number and the message is prefixed with the doctor's extension. If the extension is missing, then a message is sent back to the patient indicating that the SMS format is wrong and requesting patient 15 to resend the SMS with an extension as a prefix.

For example, a patient 15 initiates the process of obtaining an appointment using SMS by sending an SMS request for appointment in the below format: <Extension>space <APPT>space<MMM>space<DD>space<hhmm>space <AM/PM>

For example, the SMS will include the following information: "16106280648 APPT SEP 09 1415 AM".

Calendar system 25 checks the requested time availability in 15 minutes increments and if this time slot is available patient 15 will receive a reply, for example, similar to: "Your requested time /2012-09-09 14:15/ to /2012-09-09 14:30/ is available, if you want to confirm type 16106280648 APPT YES"

If patient 15 sends the reply: "16106280648 APPT YES" then, calendar system 25 will place the confirmed appointment on the calendar and a final SMS is sent as: "Your Appointment is booked"

This confirmed appointment will be viewed by a client (such as a doctor or receptionist) on the calendar as: "AUTO-<Patient Name>".

If the requested time is not available, then patient 15 will receive a SMS such as: "Sorry, Your requested time is not available, next available time is /2012-09-11 15:15/ to /2012-09-11 15:30/ if you want to confirm send 16106280648 APPT YES".

If patient 15 sends "16106280648 APPT NO" or sends nothing, no action is taken on this appointment. If patient 15 sends "16106280648 APPT YES" then calendar system 25 will place the confirmed appointment on calendar and a final SMS is sent as: "Your Appointment is booked"

A user of calendar system 25, such as doctor 14, has an option to configure the start and end time of appointment availability. Breaks also may be scheduled. If patient 15 sends appointment requests for appointments that occur outside office working hours, patient 15 will receive an SMS such as: "Sorry, Your requested time falls in our non-working hours. We work from 09:00 AM till 05:00 PM and we break from 12:00PM till 12:45 PM".

In all the cases if SMS is sent in a wrong format, an error message will be returned such as: "Wrong Format: Send <Extension> <APPT> <MMM> <DD> <hhmm> <AM/PM>".

Private network 22 allows and facilitates SMS broadcast of group announcements in accordance with predefined rules. For example, the numbering system defined within private network 22 ensures that messages will never be classified as spam and facilitates authenticated delivery of messages. This assures private network 22 is able to deliver prioritized messages in the case of a health emergency.

PHR system 30 allows for downloading of PHRs for offline or online access based on patient appointments scheduled in calendar system 25. This ensures the latest data is quickly and easily accessible to a medical doctor or other health professional addressing issues with each patient. Changes to downloaded PHRs are synchronized with records within PHR system 30. This assures that even when PHR system 30 utilizes cloud storage, PHRs are available to the health professionals even in areas where there are power outages or disruptions of Internet connection. Data integrity is verified, authenticated and further centralized into EMR system 26 where data is stored in a redundant format that assures data protection and permits recovery of any lost data.

EMR system 25 is linked to private network 22 and to calendar system 25. As PHRs are updated in PHR system 30, all changes are recorded and immediately updated to the EMR of all members of the medical support team as determined by the primary care giver. Lab requests are generated by the system and transmitted to lab reports system 28. As soon as reports are finished, the patient is alerted by SMS and a health provider via private network 22. A health provider can choose to discuss the case with other team members using private network 22, for example, via IM, internal secured e-mail, or a private voice system.

Private network 22 links health providers in a secured communication environment. This private network allows for the transfers of PHR and other confidential medical information through private network 22. This information transferred through private network 22 can be in the form of Word, PDF, TEXT, SMS, Picture, Digital X-ray, Audio, Video and any other medical approved formats. This information is directly collated into PHR system 30 based on a permission based management system. These permissions can be altered through SMS communication. This allows for a higher degree of confidentiality and privacy as per patient and doctor preferences.

Private network 22 can also be integrated with a mobile sensor based data monitoring, collection, analysis and reporting system 20. This allows for real time data collection and processing. The collected data can be placed in EMR system 26 and PHR system 30 and can also be forwarded real time to a console monitored by medical personnel. This allows the medical personnel to identify at risk patients and take appropriate medical action based, for example, on analytical graphs, and other parameters. Private network 22 can also be used to issue urgent alerts to the patient based on the collected data and on predetermined medical conditions and medically set alerts.

For example, call center 24 is an SMS call center used to provide support to all registered users with pre-assigned privilege access. This allows the provision of additional value added services to patients or other users of private network 22.

For example, private network 22 is implemented as a medical open source application integration system, which provides application program interfaces (APIs) for other developers to develop other application and integrate through a validation process with private network 22.

The foregoing discussion discloses and describes merely exemplary methods and implementations. As will be understood by those familiar with the art, the disclosed subject matter may be embodied in other specific forms without departing from the spirit or characteristics thereof. Accordingly, the present disclosure is intended to be illustrative, but not limiting, of the scope of the invention, which is set forth in the following claims.

What is claimed is:

1. A messaging system for a health care community, the messaging system comprising:
   a private network, the private network being implemented using hardware;
   electronic medical records accessible via the private network;
   a calendar system that includes appointments of patients with medical providers; and,
   an encrypted firewall and subscriber directory that limits access to the private network from a telephone network so that only subscribers to the private network have access to the private network, wherein subscribers are identified by mobile phone numbers or extensions, and wherein the encrypted firewall confirms a phone number or an extension is within the subscriber directory before allowing access from the phone number or the extension to the private network;
   wherein the calendar system receives appointment requests from subscribers to the private network via short message service communication (SMS) messages and when an open slot for a requested appointment is available within the calendar, the requested appointment is placed on the calendar and a sender of the appointment request is notified via SMS.

2. A messaging system as in claim 1 wherein the messaging system additionally comprises a personal health record system, wherein a personal health record for a patient is downloaded from a cloud storage system prior to an appointment with the patient so as to be available to medical provider during the appointment with the patient.

3. A method for making automated calendar appointments in a calendar, comprising:
   using an encrypted firewall and subscriber directory that limits access to the calendar from a telephone network so that only subscribers to a private network have access to the calendar, wherein subscribers are identified by mobile phone numbers or extensions, and wherein the encrypted firewall confirms a phone number or an extension is within the subscriber directory before allowing access from the phone number or the extension to the calendar;
   receiving, by an automated calendaring system, an appointment request within a short message service communication (SMS); and,
   when an open slot for a requested appointment is available within the calendar, so notifying a sender of the appointment request via SMS sent by the automated calendaring system and placing the requested appointment on the calendar.

4. A method as in claim 3 additionally comprising:
   ignoring the appointment request if the sender of the appointment request is not authenticated as a system subscriber.

5. A method as in claim 3 wherein notifying the sender via SMS and placing the requested appointment on the calendar includes:
   waiting for the sender to confirm the requested appointment before adding the requested appointment into the calendar.

6. A method as in claim 3 additionally comprising:
   sending an SMS reminder to the sender at a predetermined time before an occurrence of the requested appointment.

7. A method as in claim 3 wherein the appointment request within the short message service communication specifies an extension and a requested appointment time and date.

8. A method as in claim 7, additionally comprising:
   using the extension to identify the calendar.

9. A secure system comprising:
   a calendar accessible on a server using a web browser;
   an encrypted firewall and subscriber directory that limits access to the calendar from a telephone network so that only subscribers to a private network have access to the private network from the telephone network, wherein subscribers are identified by mobile phone numbers or extensions, and wherein the encrypted firewall confirms a phone number or an extension is within the subscriber directory before allowing access from the phone number or the extension to the private network; and, an SMS server that allows a subscriber to the private network to make an appointment on the calendar by sending an appointment request within a short message service communication (SMS), a requested appointment being placed on the calendar when an open slot for the requested appointment is available within the calendar.

10. A secure system as in claim 9 wherein the subscriber is required to confirm the requested appointment before the requested appointment is added into the calendar.

11. A secure system as in claim 9 wherein the SMS server sends an SMS reminder to the subscriber at a predetermined time before the occurrence of the requested appointment.

12. A secure system as in claim 9 wherein the appointment request within the short message service communication specifies an extension and a requested appointment time and date.

13. A secure system as in claim 12 wherein the SMS server uses the extension to identify the calendar.

\* \* \* \* \*